(12) United States Patent
Serrano Casasola et al.

(10) Patent No.: US 9,700,576 B2
(45) Date of Patent: Jul. 11, 2017

(54) COMBINATION OF ANTICHOLESTEROLEMIC FIBER

(71) Applicant: UNIVERSITAT DE LLEIDA, Lleida (ES)

(72) Inventors: Jose Carlos Enrique Serrano Casasola, Lleida (ES); Manuel Portero Otin, Lleida (ES); Reinaldo Pamplona Gras, Lleida (ES); Nuria Brunet Garcia, Lleida (ES)

(73) Assignee: UNIVERSITAT DE LLEIDA, Lleida (ES)

(*) Notice: Subject to any disclaimer, the term of this patent is extended or adjusted under 35 U.S.C. 154(b) by 117 days.

(21) Appl. No.: 14/655,241

(22) PCT Filed: Dec. 23, 2013

(86) PCT No.: PCT/ES2013/070921
§ 371 (c)(1),
(2) Date: Jun. 24, 2015

(87) PCT Pub. No.: WO2014/102429
PCT Pub. Date: Jul. 3, 2014

(65) Prior Publication Data
US 2015/0352139 A1 Dec. 10, 2015

(30) Foreign Application Priority Data
Dec. 24, 2012 (ES) .................. 201232016

(51) Int. Cl.
| | | |
|---|---|---|
| *A61K 36/00* | (2006.01) |
| *A61K 31/715* | (2006.01) |
| *A61K 36/68* | (2006.01) |
| *C12P 19/14* | (2006.01) |
| *C12P 19/04* | (2006.01) |
| *A61K 36/8962* | (2006.01) |
| *A61K 8/97* | (2017.01) |
| *A61K 31/05* | (2006.01) |
| *C07G 1/00* | (2011.01) |
| *A61K 31/717* | (2006.01) |
| *A61K 8/73* | (2006.01) |
| *A61Q 19/00* | (2006.01) |
| *A61K 8/02* | (2006.01) |
| *A23L 11/00* | (2016.01) |
| *A23L 19/00* | (2016.01) |
| *A23L 33/105* | (2016.01) |
| *A23L 33/22* | (2016.01) |
| *A23L 33/24* | (2016.01) |
| *A61K 9/00* | (2006.01) |

(52) U.S. Cl.
CPC ............ *A61K 31/715* (2013.01); *A23L 11/00* (2016.08); *A23L 19/00* (2016.08); *A23L 33/105* (2016.08); *A23L 33/22* (2016.08); *A23L 33/24* (2016.08); *A61K 8/027* (2013.01); *A61K 8/73* (2013.01); *A61K 8/97* (2013.01); *A61K 31/05* (2013.01); *A61K 31/717* (2013.01); *A61K 36/68* (2013.01); *A61K 36/8962* (2013.01); *A61Q 19/00* (2013.01); *C07G 1/00* (2013.01); *C12P 19/04* (2013.01); *C12P 19/14* (2013.01); *A23V 2002/00* (2013.01); *A23V 2200/00* (2013.01); *A23V 2250/21* (2013.01); *A61K 9/0056* (2013.01); *A61K 2800/10* (2013.01); *A61K 2800/522* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 2003/0134006 A1 | 7/2003 | Chukwu |
| 2004/0253327 A1 | 12/2004 | Niazi |

FOREIGN PATENT DOCUMENTS

| | | | |
|---|---|---|---|
| ES | 2130092 A1 | 6/1999 |
| ES | 2136038 A1 | 11/1999 |
| ES | 2168222 B1 | 6/2002 |
| ES | 2168223 B1 | 6/2002 |
| ES | 2259258 B1 | 9/2006 |
| ES | 2332149 T3 | 1/2010 |
| JP | 2003102417 A | * 4/2003 |
| WO | WO 99/25209 | 5/1999 |
| WO | 2007/035431 A2 | 3/2007 |
| WO | 2007/069900 A1 | 6/2007 |
| WO | 2008/007672 A1 | 1/2008 |
| WO | 2008/022857 A1 | 2/2008 |
| WO | 2010/002311 A1 | 1/2010 |
| WO | 2010/002312 A1 | 1/2010 |
| WO | 2010/045182 A2 | 4/2010 |
| WO | 2011/020853 A1 | 2/2011 |

OTHER PUBLICATIONS

International Search Report for PCT/ES2013/070921dated Apr. 17, 2014.
Benitez, et al., "Characterization of Industrial Onion Wastes", Plant Foods Hum. Nutr. (2011) 66:48-57.
Benitez, et al., "Onion (*Allium cepa* L.) by-products as source of dietary fiber: physicochemical properties and effect on serum lipid levels in high-fat fed rats", European Food Research and Technology, vol. 234, No. 4, Jan. 28, 2012, 617-625.

(Continued)

*Primary Examiner* — Qiuwen Mi
(74) *Attorney, Agent, or Firm* — KramerAmado, P.C.

(57) ABSTRACT

The present invention relates to fiber compositions comprising fiber derived from onion and soluble fiber. Additionally, the invention relates to food products comprising said fiber compositions. In another aspect, the invention relates to methods for obtaining said fiber compositions as well as to the cosmetic uses and therapeutic uses thereof in the treatment and/or prevention of metabolic diseases, colon cancer and bowel inflammation.

12 Claims, 8 Drawing Sheets

(56) References Cited

OTHER PUBLICATIONS

Dence, "The Determination of Lignin", Methods in Lignin Chemistry, 1992, 33-61.

Adom, et al., "Antioxidant Activity of Grains", J. Agric. Food Chem. 2002, 50, 6182-6187.

Downes, "Effect of curing at different temperatures on biochemical composition on onion (*Allium cepa* L.) skin from three freshly cured and cold stored UK-grown onion cultivars", Postharvest Biology and Technology 54 (2009) 80-86.

Englyst, et al., "Colorimetric Method for Routine Measurement of Dietary Fibre as Non-Starch Polysaccharides. A Comparison with Gas-Liquid Chromatography", Food Chemistry 24 (1987) 63-76.

Englyst, et al., "Improved Method for Measurement of Dietary Fiber as Non-Starch Polysaccharides in Plant Foods", J. Assoc. Off. Anal. Chem. (vol. 71, No. 4) 1988.

Jaime, et al., "Structural Carbohydrate Differences and Potential Source of Dietary Fiber of Onion (*Allium cepa* L.) Tissues", Journal of Agricultural and Food Chemistry, vol. 50, No. 1, Jan. 1, 2002, 122-128.

Lange, "Elicitor-Induced Spruce Stress Lignin", Plant Physiol. (1995) 108: 1277-1287.

Lee, et al., "Effects of daly quercetin-rich supplementation on cardiometabolic risks in male smokers", Nutrition Research and Practice 2011; 5(1): 28-33.

Prosky, et al., "Determination of Total Dietary Fiber in Foods and Food Products: Collaborative Study", J. Assoc. Off. Anal. Chem. (vol. 68, No. 4) 1985.

Terry, et al., "Effect of Water Deficit Irrigation and Inoculation with Botrytis cinerea on Strawberry (Fragaria x ananassa) Fruit Quality", J. Agric. Food Chem. 2007, 55, 10812-10819.

Vazquez-Prieto, et al., "Organosulfur compounds and cardiovascular disease", Molecular Aspects of Medicine 31 (2010) 540-545.

\* cited by examiner

COMBINATION OF ANTICHOLESTEROLEMIC FIBER

FIELD OF THE INVENTION

The present invention is encompassed within the field of prevention and treatment of diseases relating to changes in lipid profile. More specifically, the invention relates to a fiber composition formed by fiber derived from onion and soluble fiber with hypocholesterolemic, hypoglycemic and antioxidant effects.

BACKGROUND OF THE INVENTION

The use of fiber as a nutritional supplement or food additive is widely accepted and used all over the world today. This can be attributed to the general knowledge of the beneficial health effects widely described by various research projects worldwide and the knowledge that most of the population has about the term "fiber". The following can be mentioned among the beneficial effects:
- Improving and/or stabilizing colonic microbiota composition
- Improving bowel function (stool consistency, regularity of bowel evacuation, bowel transit regulation, etc.)
- Reducing the risk of suffering colon cancer
- Reducing the risk of and/or improving the handling of bowel inflammation
- Reducing the risk of bowel infection
- Modulating the working of the immune system through modifications in colonic microbiota metabolisms
- Reducing the risk of obesity, type 2 diabetes, metabolic syndrome, etc., among others.

Nevertheless, the described physiological effects are mainly determined by the composition and/or type of fiber as well as the compounds associated with it. In this sense, not all types of fibers exert all the described physiological effects, and the degree of the effect observed can also depend to a great extent on their composition and the bioactive compounds associated therewith.

In relation to blood lipid profile modification, fiber, mainly soluble fiber, is considered to exert its effects through its capacity of chelating bile salts produced in the liver through cholesterol. Additionally, it has been described that some of the by-products of colonic fermentation such as short-chain fatty acids (propionic acid, for example) could have a certain effect on the inhibition of HMGCo-A (hydroxymethylglutaryl coenzyme A reductase), a key enzyme in cholesterol synthesis.

In general terms, it can be established that the intake of 2 to 10 g of soluble fiber or viscous fibers a day is associated with a reduction of total cholesterol (−0.045 mmol/L per gram of fiber) and LDL cholesterol (−0.067 mmol/L per gram of fiber), a fact that is proven both in hypercholesterolemic and normocholesterolemic subjects. Nevertheless, HDL cholesterol levels tend to drop (−0.002 mmol/L per gram of fiber) or are not affected after dietary treatments with soluble fiber, which is undesirable according to cardiovascular risk indices. One of the main biochemical cardiovascular risk indicators is the ratio of the serum concentrations of total cholesterol (TC) and HDL, such that the lowest possible values, ideally below 4.5, are desired. The administration of dietary fiber that reduces both total cholesterol and LDL levels and HDL levels does not successfully reduce the TC/HDL ratio, and is therefore not completely effective in reducing cardiovascular risk.

There is certain evidence that some bioactive compounds, for example phytosterols, among others, can affect cholesterol flow through the intestinal epithelium by modifying the expression of the reverse flow (towards the lumen of the intestine) cholesterol transporters ABCG5 and ABCG8, thus reducing the plasma total cholesterol levels, LDL cholesterol levels and possibly increasing HDL cholesterol levels. Nevertheless, no compound that can considerably reduce LDL cholesterol levels while HDL cholesterol levels are increased has been described. For example, a recent meta-analysis describes that consuming 0.6 to 2.5 g of phytosterols a day shows a similar effect in the reduction of both LDL and HDL levels. Even though consuming foods of plant origin, the main source of fiber and bioactive compounds in diet, is known to improve the lipid profile, it is impossible to induce an increase in HDL levels when attempts are made to simulate their consumption through supplementing or other means.

Therefore, there is a need to provide fiber-based preparations capable of reducing total cholesterol and LDL levels while at the same time increasing HDL levels.

BRIEF DESCRIPTION OF THE INVENTION

Figure 5:
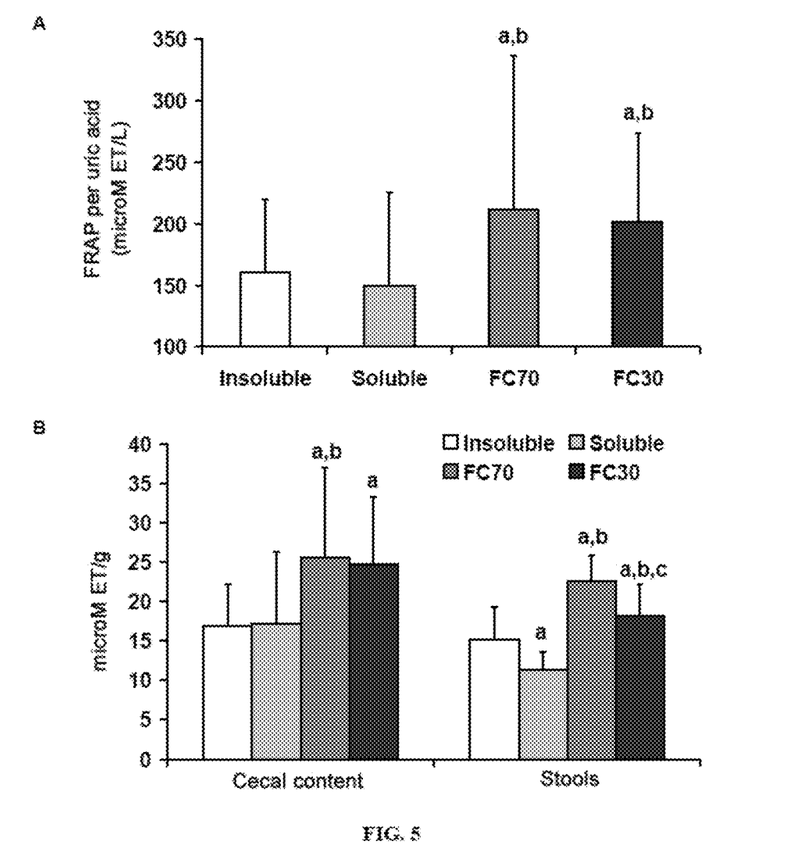
FIG. 5. Evaluation of antioxidant homeostasis. A. Plasma antioxidant capacity determined by the FRAP method. The values were corrected by the uric acid content of each sample as well as by the antioxidant capacity provided by this component. B. and C. Antioxidant capacity and polyphenol content in the cecal content and stools determined by the FRAP method and by the Folin-Ciocalteu reagent, respectively. D. Oxidative damage to tissue proteins determined in small intestine, cecum and liver samples. The oxidative damage was determined through the reactivity of carbonyl groups with respect to dinitrophenylhydrazine and was detected by Western Blot techniques. The values are presented with respect to the oxidative damage found in animals fed with insoluble fiber as the control sample.

The present invention is based on the discovery that the oral administration to mice of a product enriched in dietary fiber obtained from onion by-products derived from the food industry in combination with a soluble fiber source is capable of improving their lipid profile, reducing total cholesterol and LDL levels, and simultaneously increasing HDL levels (FIG. 3), reducing weight gain (FIG. 1B), improving glucose tolerance (FIG. 2B) and improving plasma antioxidant capacity (FIG. 5).

Therefore, in a first aspect the invention relates to a composition comprising
 a) a component A comprising an onion homogenate treated with a carbohydrase and a protease and partially dehydrated, and comprising between 75 and 95% by wet weight of insoluble fiber, and
 b) a component B comprising between 60 and 80% by wet weight of soluble fiber,
wherein the total fiber represents between 70 and 90% by weight of the total composition, and wherein said total fiber comprises between 60 and 80% by weight of insoluble fiber and between 20% and 40% by weight of soluble fiber.

In another aspect, the invention relates to a composition comprising
 a) a component A, wherein said component A is an onion homogenate comprising
  between 0.5 and 4% of soluble fiber,
  between 70 and 90% of insoluble fiber, wherein said insoluble fiber comprises between 35 and 55% of lignin and between 45 and 65% of non-starch polysaccharides,
  between 1 and 5% of soluble sugars
  between 1 and 4% of phenols
 b) a component B, wherein said component B comprises soluble fiber, wherein said soluble fiber represents between 60 and 80% of the total composition of component B,
wherein the total fiber represents between 70 and 90% of the total composition, and wherein said total fiber comprises between 60 and 80% of insoluble fiber and between 40 and 20% of soluble fiber.

In another aspect, the invention relates to a method for obtaining a product enriched in dietary fiber which comprises treating an onion homogenate with a carbohydrase and with a protease and partially dehydrating said homogenate until the proportion of insoluble fiber represents between 75% and 95% of the total composition of said product enriched in dietary fiber, as well as to a product enriched in dietary fiber obtainable by means of a method according to said method.

In another aspect, the invention relates to the use of a composition according to the invention, a food product according to the invention or a product enriched in fiber according for the preparation of a medicinal product for the prevention and/or treatment of a disease selected from a metabolic disease, colon cancer and bowel inflammation.

In another aspect, the invention relates to a cosmetic method for the treatment and/or prevention of obesity in a subject which comprises administering to said subject an effective amount of a composition, a food product or a product enriched in fiber according to the invention.

DETAILED DESCRIPTION OF THE INVENTION

Figure 1:
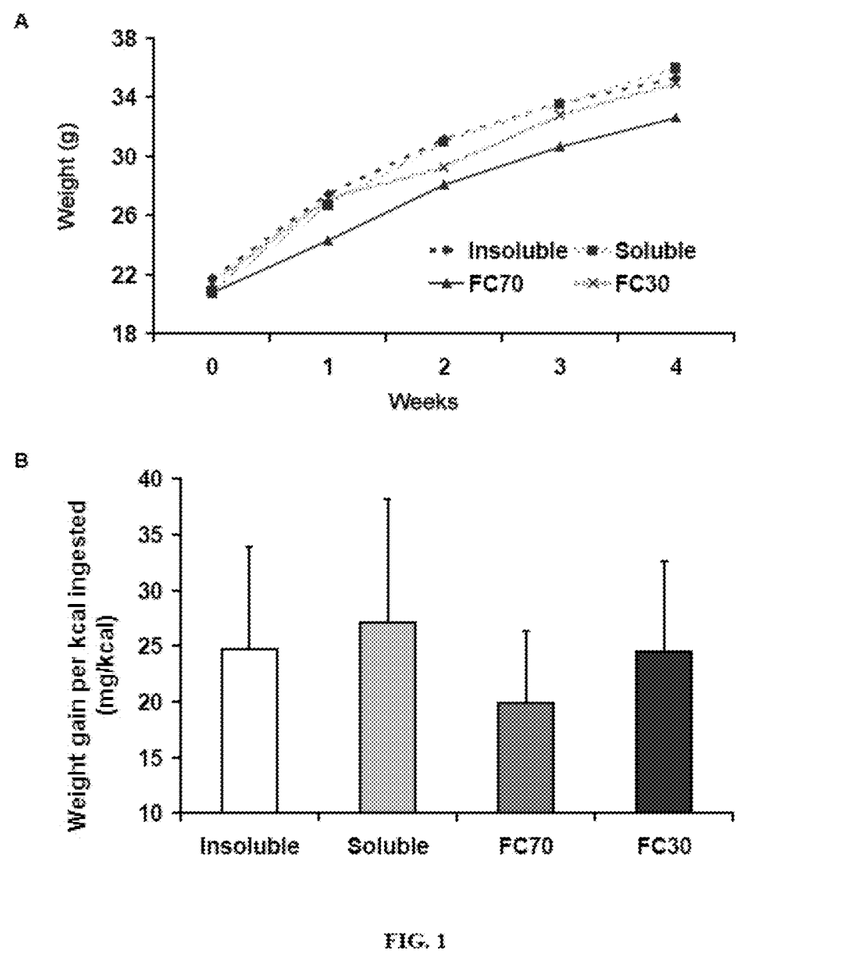
FIG. 1. Effect of the consumption of fiber FC70 on weight gain in high-calorie and high-fat diets. A. Weight gain evaluation curve and B. Average weight gain per kcal intake at the end of the study and C. Total energy intake expressed as kcal intake in the 4-week period.
Figure 2:
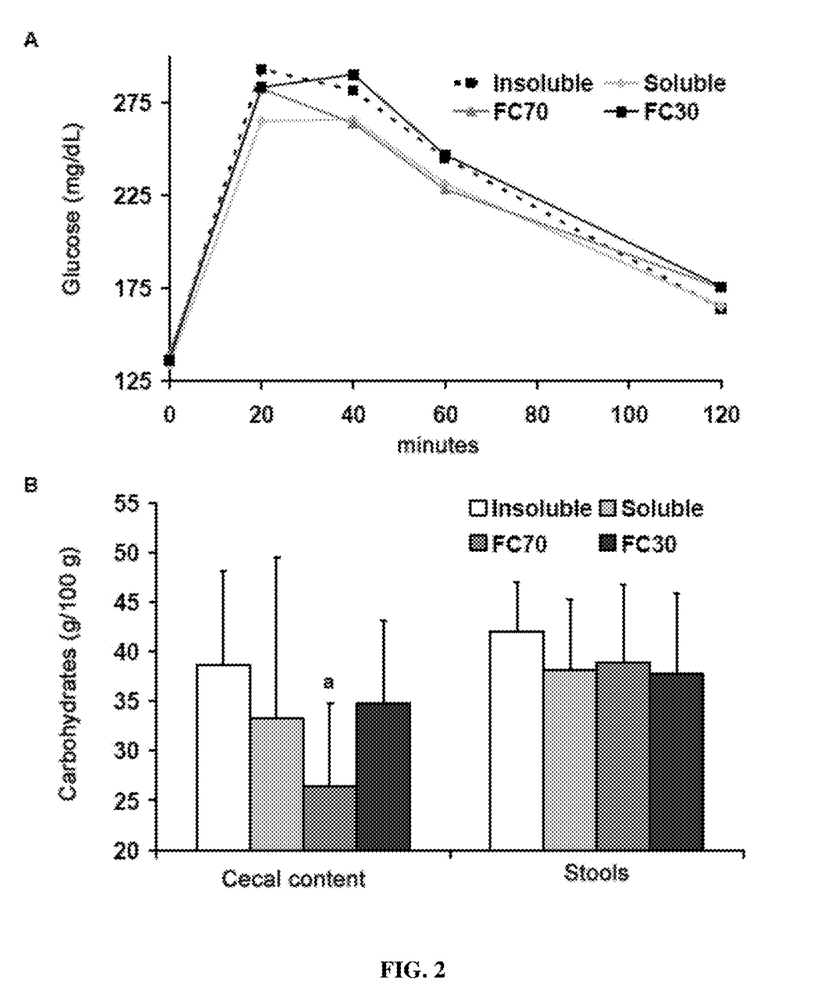
FIG. 2. Effects of the consumption of fiber FC70 on glucose homeostasis after 4 weeks of treatment. A. Subcutaneous glucose tolerance curve. Glucose was administered at a dose of 2000 mg/kg of weight subcutaneously and the increase in plasma glucose was monitored by means of tail venipuncture every 20 minutes. B. Carbohydrate content in cecal content (cecum) and stools of animals after being sacrificed. The total carbohydrates were determined from the method described by Englyst and Cummings (1988). The values are presented as grams of carbohydrates per 100 grams of stools or lyophilized cecal content.
Figure 3:
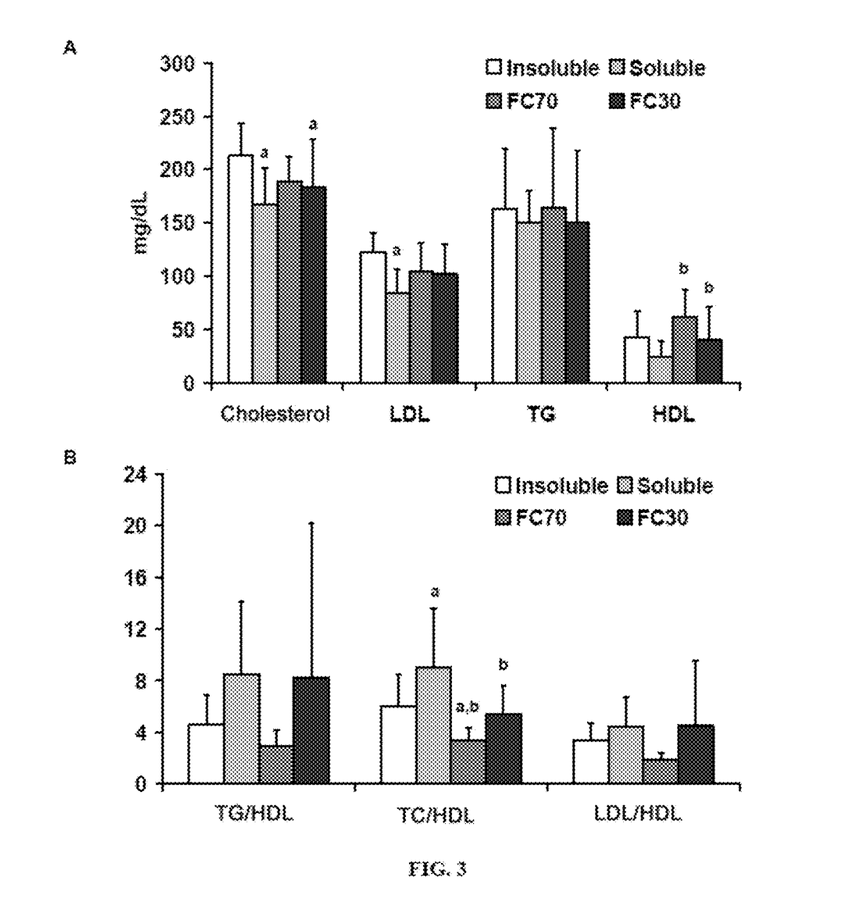
FIG. 3. Effect of the consumption of FC70 on lipid homeostasis after 4 weeks of treatment. A. Blood lipid profile determined after sacrificing the animals. B. Relationships between the different blood lipid components with the risk of insulin resistance (TG/HDL) and cardiovascular diseases (TC/HDL and LDL/HDL). C. Indigestible fat content in stools determined by the Soxhlet method based on extraction with petroleum ether.
Figure 4:
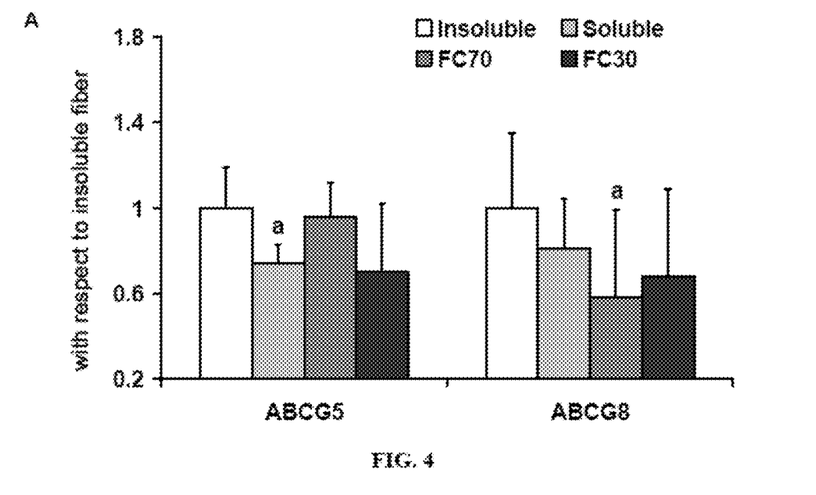
FIG. 4. Determination of the content of sterol transporters ABCG5 and ABCG8 in A. small intestine, B. cecum and C. liver. The content of transporters ABCG5 and ABCG8 in these tissues was determined by means of Western Blot technique.

The authors of the present invention have discovered that not only did the administration for 4 weeks of a product enriched in dietary fiber formed by 70% of fiber derived from onion and 30% of soluble fiber as a dietary supplement to mice fed with a high-calorie and high-fat diet reduce total cholesterol and LDL levels, but it also increased HDL levels, producing a substantial improvement in the lipid profile of the mice (FIG. 3). Without wanting to be limited to any theory in particular, it is believed that said effect results from the fact that the product is capable of modulating the flow of sterol transport to the lumen of the intestine, inducing an increase in the expression of transporter protein ABCG5 in the intestinal epithelium (FIG. 4). Additionally, the administration of said product enriched in fiber also reduced weight gain (FIGS. 1A and 1B), improved glucose tolerance (FIG. 2A) and increased plasma antioxidant capacity (FIG. 5).

The following inventive aspects have been developed based on this discovery.

Composition and Food Product of the Invention

In a first aspect, the invention relates to a composition, hereinafter first composition of the invention, comprising
  a) a component A comprising an onion homogenate treated with a carbohydrase and a protease and partially dehydrated, comprising between 75 and 95% by wet weight of insoluble fiber, and
  b) a component B comprising between 60 and 80% by wet weight of soluble fiber,
wherein the total fiber represents between 70 and 90% by weight of the total composition, and wherein said total fiber comprises between 60 and 80% by wet weight of insoluble fiber and between 20% and 40% by wet weight of soluble fiber.

Component A of the first composition of the invention comprises an onion homogenate. As used in the present description, the term "onion homogenate" refers to a substantially homogeneous preparation obtained by means of a physical or chemical treatment of the onion. A substantially homogeneous preparation is understood as any preparation having a uniform structure and composition. As used in the present description, the term "onion" refers to an herbaceous plant of the Amaryllidaceae family, the scientific name of which is *Allium cepa*. The term onion covers all the varieties of the *A. cepa* species. Illustrative, non-limiting examples of the varieties of *A. cepa* that can be used for obtaining the onion homogenate useful for the first composition of the invention include: *Allium cepa* var. *aggregatum*, *Allium cepa* var. *anglicum*, *Allium cepa* var. *argenteum*, *Allium cepa* var. *bifolium*, *Allium cepa* var. *crinides*, *Allium cepa* var. *flandricum*, *Allium cepa* var. *globosum*, *Allium cepa* var. *hispanicum*, *Allium cepa* var. *jamesii*, *Allium cepa* var. *lisboanum*, *Allium cepa* var. *luteum*, *Allium cepa* var. *multiplicans*, *Allium cepa* var. *portanum*, *Allium cepa* var. *praecox*, *Allium cepa* var. *rosum*, *Allium cepa* var. *sanguineum*, *Allium cepa* var. *solaninum*, *Allium cepa* var. *tripolitanum*, *Allium cepa* var. *viviparum*.

In a preferred embodiment, the term onion refers to the bulb of the onion plant.

The onion homogenate can be obtained from any part of the bulb of the onion plant, for example, from the darker colored outer skins, from both ends of the bulb or from any of the innermost layers of the onion. In a particular embodiment, the onion homogenate is obtained from the whole onion bulb.

The onion homogenate useful for obtaining the first composition of the invention can be obtained by means of any technique known by the person skilled in the art which allows carrying out food homogenization. The homogenization can be carried out, for example, by means of extruders, hammer mills or colloidal mills for smashing, grinding and/or breaking up the raw material. The onion homogenate can be obtained by mixing the onion with water at a ratio of 1:1 and subjecting the mixture to a temperature less than 50° C.

The onion homogenate present in component A of the first composition of the invention is treated with a carbohydrase and a protease.

As used in the present description, the term "carbohydrase" or "glycosyl hydrolase" refers to an enzyme catalyzing the hydrolysis of the glycosidic bond in carbohydrates to produce simple sugars. Carbohydrases are classified in the EC 3.2.1 family. Illustrative, non-limiting examples of carbohydrases include amylase, lactase, chitinase, galactosidase, maltase, neuraminidase, invertase, hyaluronidase and lysozyme.

In a preferred embodiment of the composition, the carbohydrase is an amylase. As used herein, the term "amylase" or "sucrase" refers to an enzyme catalyzing the hydrolysis of the 1-4 bonds of the α-amylose component present in polysaccharides, such as glycogen or starch, to produce simple sugars. The term amylase includes the enzymes α-amylase, β-amylase and γ-amylase. The amylase is preferably α-amylase. As used in the present description, the term "α-amylase" or "glycogenase" or "1,4-α-D-glucan-glucanohydrolase" refers to an enzyme identified by number EC 3.2.1.1 capable of hydrolyzing glycosidic bonds along any point of the carbohydrate chain, decomposing them to generate maltotriose and maltose from amylose and maltose, glucose and dextrin from amylopectin. The carbohydrase, preferably amylase, more preferably α-amylase, can be of any origin, for example of human origin, bovine origin, murine origin, equine origin, etc., and can be isolated from its natural source, obtained from a commercial provider or be generated in a recombinant manner.

As used in the present description, the term "protease" or "peptidase" refers to an enzyme catalyzing the hydrolysis of peptide bonds in proteins. Illustrative, non-limiting examples of proteases useful for the treatment of the onion homogenate which is part of the composition of the invention include serine peptidases, threonine peptidases, cysteine peptidases, aspartyl peptidases, metallopeptidases and glutamyl peptidases. In a particular embodiment, the protease is pepsin, trypsin or chymotrypsin. The protease is preferably pepsin. As used in the present description, the term "pepsin" refers to a protease catalyzing the hydrolysis of peptide bonds between hydrophobic amino acids and preferably aromatic amino acids, such as phenylalanine, tryptophan and tyrosine. Pepsin is a digestive enzyme secreted by the stomach where it acts on proteins, breaking them down into peptides and amino acids. Pepsin originates from its pepsinogen precursor which is hydrolyzed at acidic pH of the stomach. Pepsin is more active at a pH comprised between 2 and 3 and generally has no activity above pH 5.

The protease, preferably the pepsin, useful for the treatment of the onion homogenate can be of any origin, for example of porcine origin, humane origin, murine origin, bovine origin, equine origin, among others, and can be obtained by isolating it from its natural source, in a recombinant manner, or by acquiring one of the commercially available preparations.

The treatment of the onion homogenate with a carbohydrase and a protease can be carried out by incubating the homogenate with each of the carbohydrase and protease enzymes separately or simultaneously. In a particular embodiment, the treatment with α-amylase is carried out by incubating the homogenate with α-amylase at an α-amylase concentration between 0.05% and 0.2% with respect to the homogenized material before partial dehydration. The treatment with α-amylase is preferably carried out by incubating the homogenate with α-amylase at a concentration of 0.1% with respect to the homogenized material before partial dehydration.

In another particular embodiment, the treatment with pepsin is carried out by incubating the homogenate with pepsin at a pepsin concentration between 0.1% and 0.5% with respect to the homogenized material before partial dehydration. The treatment with pepsin is preferably carried out by incubating the homogenate with pepsin at a concentration of 0.3% with respect to the homogenized material before partial dehydration.

In a particular embodiment, the treatment with the carbohydrase and protease, preferably α-amylase and pepsin, respectively, is carried out by incubating said enzymes with the homogenate at a temperature comprised between 25° C. and 40° C., preferably at a temperature of 37° C.

In a particular embodiment, the treatment with the carbohydrase and protease, preferably α-amylase and pepsin, respectively, is carried out by incubating said enzymes with the homogenate for a time period comprised between 6 and 12 hours, preferably for 6 hours.

In a particular embodiment, the treatment with the carbohydrase and protease, preferably α-amylase and pepsin, respectively, is carried out by incubating said enzymes with the homogenate at a temperature of 37° C. for 6 hours and preferably under stirring.

The onion homogenate treated with a carbohydrase and a protease is partially dehydrated. As used herein, the term "partially dehydrated" refers to the fact that the homogenate, after its treatment with a carbohydrase and a protease, has been subjected to a drying or water removal process, such that its water content is reduced with respect to the water content before the drying process. The person skilled in the art knows the suitable techniques for carrying out the partial dehydration of the homogenate. In a preferred embodiment of the composition of the invention, the partial dehydration is carried out by means of pressing the homogenate. The process of partially dehydrating the homogenate will be performed such that the insoluble fiber content in the resulting product (component A) is between 75% and 95% by wet weight. In a particular embodiment, the process of partially dehydrating the homogenate will be performed such that the insoluble fiber content of component A is 80-85% by wet weight (i.e., a water content of 15-20% with respect to the total weight of component A).

As used in the present description, the term "fiber" or "dietary fiber" refers to a component of plant origin which is resistant to digestion and absorption in the small intestine of humans and which undergoes partial or complete fermentation in the large intestine. Fiber is chemically defined as non-starch polysaccharides and is formed by polysaccharide constituents such as cellulose, hemicellulose, pectins, gums and mucilages, and by non-polysaccharide compounds such as lignin, cutin and tannins. The term fiber includes both insoluble fiber and soluble fiber.

As used in the present description, the term "insoluble fiber" refers to a type of dietary fiber mainly formed by substances such as cellulose, hemicellulose, lignin and resistant starch that hardly retain water and are poorly fermentable, withstanding the action of the microorganisms present in the intestine. Insoluble fiber is mainly found in foods such as wheat bran, whole grains, some vegetables and generally in all cereals.

As used in the present description, the term "soluble fiber" refers to a type of dietary fiber formed by components such as inulin, pectins, gums and fructooligosaccharides that capture a lot of water and are capable of forming viscous gels, and are highly fermentable by intestinal microorganisms. Soluble fiber increases the volume of stools and reduces their consistency. Soluble fiber is mainly found in legumes, in some cereals such as oat and barley and in some fruits.

As used in the present description, the term "total fiber" refers to the sum of soluble fiber and insoluble fiber present in a specific product or composition. Therefore, for example, the total fiber of the composition of the invention is the sum of the soluble fiber and the insoluble fiber provided by both components A and B of the composition and is equal to the total dietary fiber present in the composition of the invention.

The person skilled in the art knows techniques for determining the amount of dietary fiber, soluble fiber and insoluble fiber present in a specific composition. Any official method approved by the AOAC (Scientific Association Dedicated to Excellence in Analytical Methods) can be used for analyzing the fiber in the composition of the invention or in any of its components A and B. Illustrative, non-limiting examples of methods that can be used for determining the fiber content are:

- method 985.29 for the determination of total dietary fiber (AOAC, 2007)
- method 991.42 for the determination of insoluble dietary fiber (AOAC, 2007)
- method 992.16 for the determination of total dietary fiber (AOAC, 2007)
- method 991.43 for the determination of total, soluble and insoluble fiber
- method 993.19 for the determination of soluble fiber (AOAC, 2007)
- method 993.21 for the determination of total fiber
- method 994.13 for the determination of total fiber (AOAC, 2007)

The method for obtaining component A of the composition of the invention can comprise one or more steps of washing with water followed by drying. The process of washing with water can be carried out at a temperature comprised between 25° C. and 50° C., preferably at 45° C. The process of drying can be carried out by means of pressing or by means of lyophilization. The person skilled in the art knows both drying techniques and how to apply them for obtaining component A. In a particular embodiment, the onion homogenate treated with a carbohydrase and a protease and partially dehydrated is subjected to several steps, preferably two steps, of washing with water at 45° C. followed by drying by means of pressing and a final step of drying by means of lyophilization. Regardless of the number of steps of washing and drying, the final drying of component A will be carried out such that the insoluble fiber concentration in said component A represents between 75% and 95% by wet weight of the total composition of component A, preferably between 80% and 85%.

Component B of the composition of the invention comprises between 60% and 80% by wet weight of soluble fiber, preferably 76% of soluble fiber.

In a particular embodiment, the soluble fiber present in component B of the composition of the invention comprises hemicellulose. As used in the present description, the term "hemicellulose" refers to a heteropolysaccharide formed by a heterogeneous group of polysaccharides that are in turn formed by different monosaccharides (xylose, arabinose, galactose, mannose, glucose and glucuronic acid) bound by β(1-4) bonds forming a branched linear chain. Examples of hemicelluloses that can be part of the soluble fiber of component B of the composition of the invention include xylan, glucuronoxylan, arabinoxylan, glucomannan and xyloglucan. In a preferred embodiment, the hemicellulose is arabinoxylan. As used in the present description, the term "arabinoxylan" refers to a type of hemicellulose formed by a chain of xylose units bound to one another by 1-4 bonds, many of which are substituted with arabinose residues.

Component B of the composition of the invention can be obtained from different sources of soluble fiber, among which are *Psyllium* seeds, *Avena sativa* seeds or *Ceratonia siliqua* seeds.

In a particular embodiment, component B is obtained from *psyllium* seeds. As used in the present description, the term "*Psyllium*" is the common name of several members of the plant genus *Plantago* the seeds of which are used commercially for the production of mucilage. Illustrative, non-limiting examples of plants that can be used for obtaining component B of the composition of the invention include *P. ovata* and *P. psyllium* or *P. arenaria*.

Component B of the composition of the invention can be obtained from a natural source by means of standard fiber extraction processes or they can be acquired commercially. The person skilled in the art knows the dietary fiber extraction processes that are useful for obtaining component B of the composition of the invention. Since component B contains mainly soluble fiber, soluble fiber extraction methods based on an extraction in a liquid medium based on the different solubilities of the compounds are preferred, followed by the steps of purification by filtration and of precipitation in the presence of salts or alcohol. For example, if component B is derived from *Psyllium* seeds, a standard fiber extraction process known by the person skilled in the art can be carried out for isolating from *Psyllium* seeds a product having a percentage of soluble fiber comprised between 60% and 80% by wet weight with respect to the total composition of said product, preferably 76% of soluble fiber. Alternatively, there are commercially available *Psyllium* fiber preparations that can be used as component B of the composition of the invention provided that the soluble fiber composition of said commercial preparations is comprised between 60% and 80% by wet weight of its total composition. The soluble fiber concentration in said commercial preparations is preferably 76% by wet weight with respect to its total composition.

For obtaining the composition of the invention, component B is mixed with component A and is preferably homogenized by means of a mill. Homogenization is carried out until obtaining a particle the size of which is comprised between 0.5 and 1 mm.

The composition of the invention has a total fiber concentration between 70% and 90% by weight of said composition. The composition of the invention preferably has a total fiber concentration between 85% and 90% by weight of said composition.

The composition of the invention comprises components A and B in proportions such that the total fiber of the composition comprises between 60% and 80% by weight of insoluble fiber and between 20% and 40% by weight of soluble fiber. Said proportions will vary depending on the soluble fiber and insoluble fiber composition present in component A and in component B.

In a particular embodiment, the total fiber of the composition of the invention comprises 70% of insoluble fiber and 30% of soluble fiber.

The person skilled in the art knows how to calculate the percentages of component A and component B that must be part of the composition of the invention depending on the soluble fiber and insoluble fiber composition present in component A and in component B, and depending on the amount of total fiber, soluble fiber and insoluble fiber to be obtained in the composition of the invention. By way of illustration, in a particular embodiment, if a fiber composition comprising 85% of total fiber, 70% of which is insoluble fiber and 30% of which is soluble fiber (59.5% of insoluble fiber and 25.5% of soluble fiber with respect to the total composition) is to be obtained, the proportions of each of the components A and B can be calculated by knowing the percentage of insoluble fiber in component A and the percentage of soluble fiber in component by means of the following system of equations:

$$A = \frac{59.5 \times 100}{X}$$
$$B = \frac{25.5 \times 100}{Y}$$

where
A represents the percentage of component A that will be added to the composition of the invention
B represents the percentage of component B that will be added to the composition of the invention
X represents the percentage of insoluble fiber present in component A
Y represents the percentage of soluble fiber present in component B The person skilled in the art will be able to adapt this system of equations for different embodiments in which a composition with an amount of total fiber or of insoluble and/or insoluble fiber different from those indicated in the preceding example is to be obtained. Likewise, the component A may not necessarily be the only insoluble fiber source, and similarly component B may not necessarily be the only soluble fiber source, in which case the person skilled in the art will be able to adapt the preceding system of equations such that he/she can calculate the proportions of components A and B present in the composition of the invention. There is also the possibility that the composition of the invention comprises additional components, in which case, as will be understood by the person skilled in the art, the sum of the percentages of A and B will not be equal to 100, but rather less than 100, achieving a value that will depend on the proportion represented by A and B with respect to the total composition and on the percentage of said additional components.

Additional components that can be incorporated to the compositions of the invention include, without limitation, water or aqueous solutions, starch, thickeners, dyes, flavorings, odorants, acidulants (for example, lactic acid or malic acid), sweeteners, vitamins, minerals, preservatives and others.

In a particular embodiment, the composition of the invention has a percentage of sugars by weight of less than 5%, preferably less than 4%, 3%, 2% or 1%. As used herein, the term "sugar" refers to monosaccharide and disaccharide carbohydrates. Examples of sugars are fructose, glucose, galactose, mannose, sucrose, lactose, maltose, cellobiose, etc. The determination of the amount of sugars present in the composition of the invention can be carried out by means of any suitable technique known by the person skilled in the art, such as the Lane-Eynon method (method AOAC 968.281), liquid chromatography and HPLC (High Performance Liquid Chromatography) methods, for example.

In another aspect, the invention relates to a composition, hereinafter second composition of the invention, comprising
a) a component A, wherein said component A is an onion homogenate comprising
between 0.5 and 4% of soluble fiber,
between 70 and 90% of insoluble fiber, wherein said insoluble fiber comprises between 35 and 55% of lignin and between 45 and 65% of non-starch polysaccharides,
between 1 and 5% of soluble sugars
between 1 and 4% of phenols
b) a component B, wherein said component B comprises soluble fiber, wherein said soluble fiber represents between 60 and 80% of the total composition of component B,
wherein the total fiber represents between 70 and 90% of the total composition, and wherein said total fiber comprises between 60 and 80% of insoluble fiber and between 40 and 20% of soluble fiber.

In a particular embodiment, the second composition of the invention is a composition according to the first aspect, i.e., a composition comprising
a) a component A comprising an onion homogenate treated with a carbohydrase and a protease and partially dehydrated, and comprising between 75 and 95% by wet weight of insoluble fiber, and
b) a component B comprising between 60 and 80% by wet weight of soluble fiber,
wherein the total fiber represents between 70 and 90% by weight of the total composition, and wherein said total fiber comprises between 60 and 80% by weight of insoluble fiber and between 20% and 40% by weight of soluble fiber.

The terms "onion homogenate", "total fiber", "insoluble fiber", "soluble fiber" have been defined above in relation to the second composition of the invention.

As used in the present description, the term "lignin" refers to a complex polymer which is part of the secondary cell wall in plants and some algae, filling in the spaces between cellulose, hemicellulose and pectin forming the cell wall. Lignin binds covalently to hemicellulose, cross-linking different polysaccharides and thus increasing the mechanical strength of the cell wall. Lignin is a cross-linked racemic macromolecule that is relatively hydrophobic and aromatic. Lignin is formed by three monolignol monomers that can be methoxylated to various degrees: p-coumaryl alcohol, coniferyl alcohol and sinapyl alcohol. These lignols are incorporated in the lignin in the form of phenylpropanoids. The person skilled in the art knows how to determine the lignin content of component A by means of standard techniques, for example, by means of the thioglycolysis technique (Lange B. M. et al., Plant Physiol 1995, 108(3):1277-1287) or by means of the Klason method (Dence, 1992, Methods in lignin chemistry, 33-61).

As used in the present description, the term "non-starch polysaccharide" or "NSP" refers to any polysaccharide that cannot be broken down by the enzymes present in the digestive tract of human beings. Said non-starch polysaccharides are formed by the linking of several monosaccharides by means of beta acetal linkages which, unlike the linkages binding the glucose molecules in starch, cannot be hydrolyzed by the digestive enzymes of human beings, therefore said non-starch polysaccharides are resistant to enzymatic digestion in the digestive tract. Illustrative, non-limiting examples of non-starch polysaccharides that can be part of component A of the composition of the invention include alginates, arabinoxylans, beta-glucans, cellulose, chitin, gellan, guar, inulin, pectin, xanthan. The person skilled in the art knows how to determine the non-starch polysaccharide content of component A by means of standard techniques such as the Englyst method or the enzymatic-chemical method (Englyst and Cummings, J Assoc Offic Anal Chemistry, 1988, 71: 808-814; Englyst and Hudson, Food Chem 1987, 24: 63-76) and the Prosky non-enzymatic gravimetric method (Prosky et al, J Assoc Offic Anal Chemistry, 1985, 68: 677-679), for example.

As used in the present description, the term "soluble sugar" refers to monosaccharides and disaccharides.

As used in the present description, the term "phenols" refers to aromatic alcohols made up of molecules having an —OH group bound to a carbon atom of a benzene ring (phenol) and differing in the substituents of said aromatic ring. The person skilled in the art knows the techniques for determining the total phenol content. For example, to determine the total phenol content in component A of the composition of the invention a phenolic compound extraction can be carried out as described by Downes et al. (Downes et al, 2009, Postharvest Biol Technol, 54: 80-86) followed by a determination according to the method described by Terry et al. (Terry et al., 2007, J Agric Food Chem, 55: 10812-10819).

In a particular embodiment, the phenols are extractable phenols. As used in the present description, the term "extractable phenols" refers to those phenols that can be solubilized in aqueous-organic solvents as opposed to non-extractable phenols, which are those retained in the resulting residue after the aqueous-organic extraction. Extractable phenols have low or medium molecular weight (from monomers to decamers). The person skilled in the art knows techniques for determining the extractable phenol concentration which are generally techniques including a first extraction with aqueous-organic solvents that allow obtaining an extract with a mixture of different polyphenolic compounds. An example is the technique described by Antovovich et al. (Antolovich et al, 2000. J Agric Food Chem, 50(21): 6182-6187).

In a particular embodiment, the phenols are hydrolyzable phenols. As used in the present description, the term "hydrolyzable phenols" or "hydrolyzable tannins" refers to readily hydrolyzable heterogeneous polymers formed by phenolic acids, particularly gallic acid, and simple sugars. Illustrative, non-limiting examples of hydrolyzable phenols include gallotannins, ellagitannins, benzoic acids and hydroxycinnamic acids.

In a particular embodiment, component A of the second composition of the invention comprises 1.5% of soluble fiber.

In another particular embodiment, component A of the second composition of the invention comprises 80% of insoluble fiber.

In another particular embodiment, the insoluble fiber of component A of the second composition of the invention comprises 43% of lignin. The lignin is preferably Klason lignin.

In another particular embodiment, the insoluble fiber of component A of the second composition of the invention comprises 57% of non-starch polysaccharides.

In another particular embodiment, the insoluble fiber of component A of the second composition of the invention comprises 43% of lignin and 57% of non-starch polysaccharides.

In another particular embodiment, component A of the second composition of the invention comprises 1.7% of soluble sugars.

In another particular embodiment, component A of the second composition of the invention comprises 2.6% of phenols.

In another particular embodiment, component B of the second composition of the invention comprises 76% of soluble fiber.

In another particular embodiment, the total fiber represents 80% of the second composition of the invention.

In another particular embodiment, the total fiber present in the second composition of the invention is formed by 70% of insoluble fiber and 30% of soluble fiber.

In another particular embodiment of the second composition of the invention
  a) component A comprises
    1.5% of soluble fiber
    80% of insoluble fiber, wherein said insoluble fiber comprises 43% of lignin and 57% of non-starch polysaccharides
    1.7% of soluble sugars
    2.6% of phenols
  b) component B comprises 76% of soluble fiber,
wherein the total fiber represents 80% of the total composition, and wherein said total fiber comprises 70% of insoluble fiber and 30% of soluble fiber.

In a particular embodiment, the onion homogenate of component A of the second composition of the invention is obtained from the whole onion bulb.

In a particular embodiment, the soluble fiber of component B of the second composition of the invention comprises hemicellulose, preferably arabinoxylan. The terms "hemicellulose" and "arabinoxylan" have been described above in the context of the first composition of the invention.

In a particular embodiment, component B is obtained from *Psyllium* seeds. The term "*Pysllium*" has been described above in the context of the first composition of the invention.

In another aspect, the present invention relates to a food product comprising the first or second composition of the invention.

As used in the present invention, the term "food product" refers to any substance or product of any nature, solid or liquid, natural or transformed, which due to its characteristics, applications, components, preparation and state of preservation, can be commonly or ideally used for any of the following purposes: a) for normal human or animal nutrition or indulgence; or b) as dietetic products in special cases of human or animal diet. The food product of the invention will preferably be a ready-to-eat food product, which is one that does not have to be diluted by means of an aqueous solution suitable for consumption, for example. In principle, the ingredients present in a ready-to-eat food product are balanced and adding additional ingredients to the food product to make it ready to eat, as is considered by a person skilled in the art, is not necessary. The food product of the invention can also be a concentrated food product, which is one in which one or more ingredients are present at a higher concentration than in a ready-to-eat food product, so to use the product it is necessary to dilute it by means of an aqueous solution suitable for consumption, for example. Illustrative, non-limiting examples of food products provided by this invention include baked goods, pastries and confectionery, cereals, chocolates, jams, juices, other fruit derivatives, oils and margarines, prepared dishes, dairy products, etc.

Method for Obtaining a Product Enriched in Dietary Fiber

In another aspect, the invention relates to a method, hereinafter first method of the invention, for obtaining a product enriched in dietary fiber which comprises treating an onion homogenate with a carbohydrase and with a protease and partially dehydrating said homogenate until the proportion of insoluble fiber represents between 75% and 95% of the total composition of said product enriched in dietary fiber.

The terms "onion homogenate", "carbohydrase", "protease", "insoluble fiber", "dietary fiber" have been described above in the context of the first composition of the invention. The particular and/or preferred embodiments of the first method of the invention are the same as those described for the first composition of the invention.

In a preferred embodiment, the homogenate is partially dehydrated until the proportion of insoluble fiber represents 80% of the total composition of the said product enriched in dietary fiber. In a preferred embodiment, the onion homogenate is a homogenate obtained from the whole onion bulb. In a preferred embodiment, the partial dehydration of the homogenate is carried out by means of pressing the homogenate.

In a preferred embodiment, the carbohydrase is an amylase. In an even more preferred embodiment, the amylase is α-amylase. In a preferred embodiment, the treatment of the onion homogenate with α-amylase is carried out at a concentration of between 0.05% to 0.2% with respect to the homogenized material before partial dehydration. In another preferred embodiment, α-amylase is used at a concentration of 0.1% with respect to the homogenized material before partial dehydration.

In a preferred embodiment, the protease is pepsin. In an even more preferred embodiment, pepsin is used at a concentration of between 0.1% to 0.5% with respect to the homogenized material before partial dehydration. In another preferred embodiment, pepsin is used at a concentration of 0.3% with respect to the homogenized material before partial dehydration.

In a preferred embodiment, the treatment of the onion homogenate with α-amylase and pepsin is carried out at a temperature comprised between 25 and 40° C. and/or for a time period comprised between 6 and 12 hours.

In another preferred embodiment, the method additionally comprises one or more steps of washing with water followed by drying.

In another preferred embodiment, the method comprises mixing the product obtained with a second component comprising between 60% and 80% by wet weight of soluble fiber, wherein the total fiber represents between 70 and 90% by weight of the total composition, and wherein said total fiber comprises between 60 and 80% by weight of insoluble fiber and between 20% and 40% by weight of soluble fiber. In another even more preferred embodiment, the second component comprises 76% by wet weight of soluble fiber, the total fiber represents between 85% and 90% of the total composition and the total fiber comprises 70% of insoluble fiber and 30% of soluble fiber. In another preferred embodiment, the soluble fiber of the second component comprises hemicellulose. In another preferred embodiment, the hemicellulose is arabinoxylan. In a preferred embodiment, the second component is obtained from *Psyllium* seeds.

The first method of the invention allows obtaining a product enriched in dietary fiber. Therefore, in another aspect the invention relates to a product enriched in dietary fiber obtainable by means of the first method of the invention.

Therapeutic Uses of the Invention

The inventors have observed that the administration of the composition of the invention to CD1 Swiss mice fed with a high-calorie and high-fat diet caused a reduced weight gain (FIG. 1), an increased glucose tolerance (FIG. 2), an improved lipid profile with a reduction of serum total cholesterol and LDL levels and an increase in HDL levels (FIG. 3) and an increased plasma antioxidant capacity (FIG. 5) compared to mice fed with insoluble fiber or to mice fed with soluble fiber.

Therefore, in another aspect the invention relates to any of the compositions of the invention, to a food product comprising any of the compositions of the invention or to a product enriched in dietary fiber obtainable by the first method of the invention for use in medicine.

In another aspect, the invention relates to any of the compositions of the invention, to a food product comprising any of the compositions of the invention or to a product enriched in dietary fiber obtainable by the first method of the invention for use in the treatment of a disease selected from a metabolic disease, colon cancer and bowel inflammation.

In another aspect, the invention relates to a therapeutic method for the treatment and/or prevention of a metabolic disease, colon cancer and bowel inflammation which comprises administering to a patient any of the compositions of the invention, a food product comprising any of the compositions of the invention or a product enriched in dietary fiber obtainable by the first method of the invention.

In another aspect, the invention relates to a use of any of the compositions of the invention, of a food product comprising any of the compositions of the invention or of a product enriched in dietary fiber obtainable by the first method of the invention for the preparation of a medicinal product for the prevention and/or treatment of a disease selected from a metabolic disease, colon cancer and bowel inflammation.

As used in the present invention, the term "metabolic disease" refers to any type of disorders in which metabolic errors and imbalances occur and in which the metabolic processes take place in a sub-optimal manner. The expression also refers to disorders that can be treated by means of modulating metabolism although the disease per se may not have been caused by a metabolic impairment. In a preferred embodiment, the metabolic disease is selected from the group consisting of hyperglycemia, type 2 diabetes, obesity, dyslipidemia and hypercholesterolemia.

As used in the present invention, the term "hyperglycemia" refers to a condition in which there are abnormally high blood glucose levels in relation to fasting baseline levels. Specifically, hyperglycemia is understood as when fasting blood glucose levels are consistently greater than 126 mg/dL, postprandial glucose levels are greater than 140 mg/dL and/or venous plasma glucose levels 2 hours after the administration of a dose of glucose of 1.75 grams per kilogram of body weight are greater than 200 mg/dL.

As used in the present invention, the term "type 2 diabetes" refers to a disease characterized by an inappropriate increase of blood glucose levels generating chronic complications due to the effect on large and small vessels and nerves. The underlining impairment in this disease is the difficulty for insulin to act (as a result of the tissues losing sensitivity to this hormone), called insulin resistance, and an inadequate secretion of insulin by the cells responsible for insulin production in the pancreas. In addition to an increased glucose concentration, deficient insulin action often translates into increased cholesterol and/or triglyceride levels.

As used in the present invention, the term "obesity" refers to the definition of obesity provided by the WHO based on the body mass index (BMI) consisting of the ratio between the weight of a person (in kg) and the square of his/her height in meters. According to this criterion, a BMI of less than 18.5 kg/m$^2$ is considered underweight or thin, a BMI of 18.5-24.9 kg/m$^2$ is considered normal weight, a BMI of 25.0-29.9 kg/m$^2$ is considered Class 1 overweight, a BMI of 30.0-39.0 kg/m$^2$ is considered obesity or Class 2 overweight, and a BMI higher than or equal to 40.0 kg/m$^2$ is considered morbid obesity. Alternatively, there are others methods to define the degree of obesity of an individual such as the diameter of the waist measured at the midpoint between the lower limit of the ribs and the upper limit of the pelvis (in cm), thickness of skin folds and bioimpedance, based on the principle that lean mass transmits electricity better than fatty mass.

As used in the present invention, the term "dyslipidemia" refers to any pathological condition characterized by lipid metabolism impairment, with subsequent changes in the concentrations of lipids (cholesterol, triglycerides and the like) and lipoproteins (high density lipoproteins) in the blood. Dyslipidemias that can be treated with the methods of the present invention include, without limitation, hypercholesterolemia, hypertriglyceridemia, hyperlipoproteinemia type I, IIa, IIb, III, IV, V, hyperchylomicronemia, combined hyperlipidemia, etc.

As used in the present invention, the term "hypercholesterolemia" refers to a pathological condition characterized by the presence of high blood cholesterol levels, particularly total cholesterol and/or LDL levels. As used herein, the term total cholesterol refers to the sum of the sub-fractions of LDL (low density lipoprotein), HDL (high density lipoprotein) and VLDL (very low density lipoprotein) cholesterol. The person skilled in the art knows the reference values of the blood total cholesterol and LDL levels, which will vary depending on different circumstances such as age, gender, etc., and will know how to determine in each case if a subject suffers hypercholesterolemia.

The term "colon cancer" refers to any malignant proliferative disorder of cells in the colon, rectum and appendix. The term colon cancer includes any of the following stages of the disease:
Stage 0: Very early cancer in the innermost layer of the intestine
Stage 1: Cancer in the inner layers of the colon
Stage 2: Cancer spread through the muscle wall of the colon
Stage 3: Cancer spread to the lymph nodes
Stage 4: Cancer has spread to other organs As used in the present description, the term "bowel inflammation" or "inflammatory bowel disease" refers to a generally chronic inflammation disorder in the colon and/or small intestine. The main forms of bowel inflammation are Crohn's disease and ulcerous colitis, although there are other forms such as collagenous colitis, lymphocytic colitis, ischemic colitis, diversion colitis, Behçet's disease and indeterminate colitis. In general, bowel inflammation is characterized by abdominal pain, diarrhea, rectal bleeding and weight loss.

The therapeutic uses and methods of the present invention involve administering to a subject a therapeutically effective amount of the composition of the invention or of the food product comprising the compositions of the invention, or of the product enriched in dietary fiber obtainable by the first method of the invention.

"Therapeutically effective amount" is understood as the amount of composition, food product comprising said composition or product enriched in fiber enriched according to the first method of the invention, which allows completely or partially relieving the symptoms associated with a metabolic disease, colon cancer or bowel inflammation, or which prevents the symptoms from progressing or worsening, or which prevents the onset of the disease in a subject at risk of suffering the disease.

As used in the present description, the term "subject" includes living organisms, such as male or female human beings, and of any race or age; animals, for example monkeys, cows, sheep, horses, pigs, goats, dogs, cats, mice, rats and transgenic species thereof. In a preferred embodiment, the subject is a human being.

The amount of active agent, specifically the amount of the composition of the invention, of food product comprising the composition of the invention or of product enriched in dietary fiber obtainable by the first method of the invention, that will be effective for the treatment and/or prevention of a metabolic disease, colon cancer or bowel inflammation, can be determined by standard clinical techniques which will depend on the disease to be treated. Optionally, in vitro assays can be used to help identify optimal dose ranges. The effective doses can be extrapolated from dose-response curves derived from test model systems in vitro or in animals.

The composition of the invention or of the food product comprising the compositions of the invention, or of the product enriched in dietary fiber obtainable by the first method of the invention, will be administered orally.

Cosmetic Uses of the Invention

The compositions of the invention or the food products comprising the compositions of the invention, or the products enriched in dietary fiber obtainable by the first method of the invention, are useful both for the treatment of morbid obesity and for the treatment of Class 1 or Class 2 overweight, in which case the methods of the invention have a cosmetic purpose. Therefore, in another aspect the invention relates to a cosmetic method for the treatment and/or prevention of obesity in a subject which comprises administering to said subject an effective amount of the composition of the invention, of food product comprising the composition of the invention or of product enriched in dietary fiber obtainable by the first method of the invention.

"Effective amount" is understood as the amount of composition, food product comprising said composition or product enriched in fiber obtainable according to the first method of the invention, which allows completely or partially relieving the symptoms associated with obesity, or preventing the symptoms from progressing or worsening or preventing the onset of obesity in a subject at risk of suffering said obesity.

In this embodiment, the subjects who have excess weight in the form of fat and who can be treated by means of the cosmetic method of the present invention are identified visually or because they have a BMI higher than or equal to 25 kg/m$^2$, preferably between 25 and 30. These individuals are considered obese that require weight control for cosmetic reasons.

EXAMPLES

Materials and Methods

To evaluate the effects of the invention, an in vivo study in a murine model with 4-week old CD1 Swiss mice that are individually caged to control their dietary intake is presented. Said animals were fed for a 4-week period with a high-calorie and high-fat diet (5.19 kcal/g; 60% of the energy in the form of fat) in which the formulation, called FC70, was incorporated at a dose of 5% of the total of the diet. Formulation FC70 is made up of 70% of onion homogenate enriched in fiber and 30% of *Psyllium* fiber. A group with insoluble fiber (cellulose) and another group with soluble fiber (*Psyllium plantago*) were included as controls in the experimentation. Additionally, another experimental group, FC30, made up of 30% of onion homogenate enriched in fiber and 70% of *Psyllium* fiber was incorporated to confirm the differential effects of the proposed formulation.

Results

Example 1: Effect on Weight Gain

Weight gain in the animals was monitored weekly throughout the entire research period. The effects of the described formulation on weight are based on a reduction of weight gain compared to the insoluble and soluble fiber controls from the first week of treatment (FIG. 1A), a difference sustained throughout the entire research period. Additionally, it is observed that the reduction of weight gain is not related to dietary intake (FIG. 1C), as well as weight gain due to energy intake (FIG. 1B), which are related to a lower bioavailability of energy or an increase in energy expenditure.

Example 2: Effects on Glucose Homeostasis

To evaluate the effects of formulation FC70 on glucose homeostasis, subcutaneous glucose (2000 mg/kg weight) tolerance curves, as well as the determination of total carbohydrate content in the cecal contents and stools after 4 weeks of treatment were carried out. The glucose tolerance curve demonstrates that the formulation confers protection in increases in glycaemia after exogenous glucose exposure (FIG. 2A). Additionally, the indigestible carbohydrate content analyzed in the cecal content and stools decreased in animals treated with formulation FC70 compared to the insoluble fiber group (FIG. 2B). This situation is related to an increase in the rate of fermentability by colonic bacteria that is primarily determined by the soluble fiber content and the polyphenols associated therewith.

Example 3: Effects on Blood Lipid Profile

The changes in lipid profile induced due to formulation FC70 are mainly evidenced by a reduction of total cholesterol and LDL levels and a significant increase in HDL cholesterol levels (FIG. 3A). The changes in lipid profile induced significant changes in total cholesterol/HDL ratios, a recognized cardiovascular risk biomarker. As can be observed in the same drawings, although the soluble fiber induces reductions in the levels of most of the lipid profile components, it also induced a drop in HDL cholesterol, which leads to unfavorable total cholesterol/HDL, TG/HDL and LDL/HDL ratios. In contrast, formulation FC70 induces a reduction in most of the lipid profile components with the exception of HDL cholesterol, which was increased.

Additionally, FC70 fiber showed a higher indigestible fat content compared to insoluble fiber (FIG. 3C); this effect was also observed both in the soluble fiber and in FC30, so it is not considered a distinguishing characteristic of FC70 fiber.

In relation to the mechanism of action whereby FC70 fiber induces this change in lipid profile, this is related to the modifications observed in the cholesterol transporters both at the intestinal epithelium level and the hepatic epithelium level (FIG. 4). Generally, compared to soluble fiber, FC70 fiber induces an increase in the content of transporter ABCG5 both at the intestinal epithelium level (FIGS. 4A and 4B) and the hepatic epithelium level (FIG. 4C), which induces a greater flow of sterols towards the lumen of the intestine and justifies the changes observed in relation to circulating HDL cholesterol levels.

Example 4: Effects on Plasma Antioxidant Capacity

Since FC70 fiber is a source of antioxidant compounds such as polyphenols and organosulfur compounds, it induces changes in blood antioxidant capacities, as well as in the cecal content during the colonic fermentation process (FIGS. 5A and 5B, respectively). In relation to the plasma antioxidant capacity, the values presented indicate the reducing capacity corrected by the values of uric acid (the main plasma antioxidant), showing that the increase induced by FC70 and FC30 fibers is directly related to the polyphenol content and the antioxidant capacity in formulations FC70 and FC30, FC70 being the formulation with a higher polyphenol content and antioxidant capacity, and it is therefore the formulation which produces a greater increase in plasma antioxidant capacity.

In relation to the increase in the antioxidant capacity observed in the cecal content and stools (FIG. 5B), they are also directly related to the higher polyphenol content observed in the same samples (FIG. 5C), originating from formulations FC70 and FC30. In that sense, a dose-response effect can be observed (FC70 higher antioxidant content and FC30 lower antioxidant content) in the samples analyzed both for antioxidant capacity and for the total polyphenol content.

Finally, the changes observed both in the plasma antioxidant capacity and in the cecal contents and stools are related to reduced oxidative damage in the small intestine and cecum measured by Western Blot (FIG. 5D); a highly distinguishing factor compared to the other types of fiber analyzed, such as soluble and insoluble fibers, which induces increased oxidative damage in the small intestine and cecum.

The invention claimed is:

1. A composition comprising
   a) a component A comprising an onion homogenate treated with a carbohydrase and a protease and partially dehydrated, and comprising between 75 and 95% by wet weight of insoluble fiber, and
   b) a component B comprising between 60 and 80% by wet weight of soluble fiber,
      wherein the total fiber represents between 70 and 90% by weight of the total composition, and wherein said total fiber comprises between 60 and 80% by weight of insoluble fiber and between 20% and 40% by weight of soluble fiber.

2. A composition comprising
   a) a component A, wherein said component A is an onion homogenate comprising
      between 0.5 and 4% of soluble fiber,
      between 70 and 90% of insoluble fiber, wherein said insoluble fiber comprises between 35 and 55% of lignin and between 45 and 65% of non-starch polysaccharides, between 1 and 5% of soluble sugars
between 1 and 4% of phenols
b) a component B, wherein said component B comprises soluble fiber, wherein said soluble fiber represents between 60 and 80% of the total composition of component B,
wherein the total fiber represents between 70 and 90% of the total composition, and wherein said total fiber comprises between 60 and 80% of insoluble fiber and between 40 and 20% of soluble fiber.

3. The composition according to claim 2, wherein
a) component A comprises
1.5% of soluble fiber
between 80% and 85% of insoluble fiber, wherein said insoluble fiber comprises 43% of lignin and 57% of non-starch polysaccharides
1.7% of soluble sugars
2.6% of phenols
b) component B comprises 76% of soluble fiber,
wherein the total fiber represents between 85% and 90% of the total composition, and wherein said total fiber comprises 70% of insoluble fiber and 30% of soluble fiber.

4. The composition according to claim 2, wherein the phenols are extractable phenols and/or hydrolyzable phenols.

5. The composition according to claim 2, wherein component A is a homogenate which is obtained from the whole onion bulb.

6. The composition according to claim 2, wherein the soluble fiber of component B comprises hemicellulose.

7. The composition according to claim 6, wherein the hemicellulose is arabinoxylan.

8. The composition according to claim 2, wherein component B is obtained from the seeds of a plant of the *Plantago* genus.

9. A food product comprising a composition according to claim 1.

10. A therapeutic method for the treatment and/or prevention of a disease selected from a metabolic disease, colon cancer and bowel inflammation which comprises administering to a patient the composition according to claim 2.

11. The method according to claim 10, wherein the metabolic disease is selected from the group consisting of hyperglycemia, type 2 diabetes, obesity, dyslipidemia and hypercholesterolemia.

12. A cosmetic method for the treatment and/or prevention of obesity in a subject which comprises administering to said subject an effective amount of a composition according to claim 2.

* * * * *